United States Patent [19]
Wiesenberg et al.

[11] Patent Number: 5,958,683
[45] Date of Patent: Sep. 28, 1999

[54] SCREENING METHOD USING THE RZR RECEPTOR FAMILY

[75] Inventors: Irmgard Wiesenberg, Weil am Rhein, Germany; Martin Missbach, Rheinfelden, Switzerland

[73] Assignee: Novartis Corporation, Summit, N.J.

[21] Appl. No.: 08/696,900

[22] PCT Filed: Mar. 18, 1995

[86] PCT No.: PCT/EP95/01017

§ 371 Date: Aug. 22, 1996

§ 102(e) Date: Aug. 22, 1996

[87] PCT Pub. No.: WO95/27202

PCT Pub. Date: Oct. 12, 1995

[30] Foreign Application Priority Data

Mar. 30, 1994 [EP] European Pat. Off. .............. 94810196

[51] Int. Cl.$^6$ .............................. C12Q 1/68; C12P 19/34; C12N 15/63; C07H 21/04
[52] U.S. Cl. .......................... 435/6; 435/91.4; 435/320.1; 435/325; 536/23.1; 536/24.1
[58] Field of Search .......................... 435/6, 91.4, 320.1, 435/325; 514/44; 536/23.1, 24.1

[56] References Cited

U.S. PATENT DOCUMENTS

| | | | |
|---|---|---|---|
| 3,746,717 | 7/1973 | Meisels et al. | 548/185 |
| 5,151,446 | 9/1992 | Horn et al. | 514/617 |
| 5,206,377 | 4/1993 | McAfee | 548/253 |
| 5,272,141 | 12/1993 | Fraschini et al. | 514/178 |
| 5,283,343 | 2/1994 | Dubocovich et al. | 548/496 |
| 5,403,851 | 4/1995 | D'Orlando et al. | 514/364 |
| 5,750,557 | 5/1998 | Zisapel et al. | 514/415 |

FOREIGN PATENT DOCUMENTS

| | | |
|---|---|---|
| 0085275 | 8/1983 | European Pat. Off. . |
| 0325849 | 8/1989 | European Pat. Off. . |
| 0447285 | 9/1991 | European Pat. Off. . |
| 0494047 | 7/1992 | European Pat. Off. . |
| 0506539 | 9/1992 | European Pat. Off. . |
| 0508955 | 10/1992 | European Pat. Off. . |
| 0527687 | 2/1993 | European Pat. Off. . |
| 0530087 | 3/1993 | European Pat. Off. . |
| 0548017 | 6/1993 | European Pat. Off. . |
| 0548018 | 6/1993 | European Pat. Off. . |
| 0562956 | 9/1993 | European Pat. Off. . |
| 565 296 | 10/1993 | European Pat. Off. . |
| 0578620 | 1/1994 | European Pat. Off. . |
| 0585206 | 3/1994 | European Pat. Off. . |
| 0591057 | 4/1994 | European Pat. Off. . |
| 2632747 | 2/1977 | Germany . |
| 0511877 | 10/1971 | Switzerland . |
| 9216546 | 10/1992 | WIPO . |
| 9216658 | 10/1992 | WIPO . |

OTHER PUBLICATIONS

Jung, et al.; Chem. Abst., vol. 117:8383g, (1992).
Missbach, M.; Chem. Abst., vol. 119:249942K, p. 983, (1993).
Andrieux, et al.; Chem. Abst., vol. 116:20792b, p. 550, (1992).
Yous, et al.; Chem. Abst., vol. 118:234044z, p. 1002, (1993).
Feige, et al.; Chem. Abst., vol. 117:220078f, p. 524 (1992).
Le sieur, et al.; Chem. Abst., vol. 119:8521s, p. 874 (1993).
Langlois, et al.; Chem. Abst., vol. 121:82734w, p. 1044 (1994).
Missbach, M.; Chem. Abst., vol. 119:271154b, p. 998, (1993).
Yous, et al.; Chem. Abst., vol. 120:1065662, p. 1111 (1994).
Lesieur, et al.; Chem. Abst., vol. 118:254750e, p. 806 (1993).
Gowan, et al.; Molec. And Cellular Biol., vol. 2(9):1044–1051, (1982).
Schneider, I.; J. Embryol. Exp. Morp. vol. 27(2):353–365, (1972).
Luckow, et al.; Nucleic Acids Res., vol. 15(13): p. 5490, (1987).
Becker–Andre, et al.; (Abst.) Keystone Symposium, K402, p. 376, (1994).
Becker–Andre, et al.; Biochemical and Biophysical Research Communications, vol. 194, No. 3, (1993), pp. 1371–1379.
Graupner, et al.; Biochemical and Biophysical Research Communications, vol. 179, No. 3, (1991), pp. 1554–1561.
Luyten, et al.; TIBTECH, vol. 11, (1993), pp. 247–254.
McDonnell, et al.; Biotechnology, vol. 11, (1993), pp. 1256–1261.
Wiesenberg, et al.; Nucleic Acids Research, vol. 23, No. 3, (1995), pp. 327–333.
Becker–Andre, et al.; Journal of Biological Chemistry, vol. 269, No. 46, (1994), pp. 28531–28534.
Hirose, et al.; Biochemical and Biophysical Research Communications, vol. 205, No. 3, (1994), pp. 1976–1983.
O'Malley, et al.; Molec. Endocrinol., vol. 6:pp. 1359–1361, (1992).
Wiesenberg, et al.; Clin. Exp. Immunol., vol. 78: pp. 245–249; (1989).
Ebisawa, et al.; Proc. Nat'l. Acad. Sci., vol. 91:6133–6137, (1994).
Jung, et al.; Angewandte Chemie, vol. 104:375–391, (1992).
Reppert, et al.; Neuron, vol. 13:1177–1185, (1994).
Forman, et al.; Molecular Endocrinol., vol. 8(9): pp. 1253–1261, (1994).
Retnakaran, et al.; Molecular Endocrinology, vol. 8(9):1234–1244, (1994).

(List continued on next page.)

*Primary Examiner*—Nancy Degen
*Assistant Examiner*—William Sandals
*Attorney, Agent, or Firm*—Gregory D. Ferraro

[57] ABSTRACT

The current invention concerns the use of a receptor from the RZR/ROR receptor family or a functional fragment thereof in a test of a compound for anti-autoimmune, anti-arthritic, anti-tumor, melatonin-like and or melatonin-antagonistic activity and the production of a receptor ligand complex comprising the receptor or a functional fragment thereof and a ligand of the receptor. Also described is a method for testing compounds for said activity (screening for ligands) and the active compounds identified therewith.

23 Claims, No Drawings

OTHER PUBLICATIONS

Carlberg, et al.; Molec. Endocrinol., vol. 8:757–770, (1994).
Garrett, et al.; Bioorg. and Medicinal Chem. Lett., vol. 4(13):1559–1564 (1994).
Depreux, et al.; J. Med. Chem., vol. 37:3231–3239, (1994).
Schieweck, et al.; 13th Int'l Congress of Chemotherapy, Vienna, Austria, vol. 16:66–70, Aug. 28–Sep. 2, 1983.
Copinga, et al.; J. Med. Chem., vol. 36:2891–2898, (1993).
Carlberg, et al.; Nature, vol. 361:657–660, (1993).
Hall, et al.; Proc. Nat'l. Acad. Sci., vol. 90:6929–6933, (1993).
Williams, M.; Current Opin. Biotechnol., vol. 4:85–90, (1993).
Giguere, et al.; Genes and Devel., vol. 8:538–553, (1994).
Schmidt–Ruppin.; Experientia, vol. 29(7):823–825, (1973).
Kerr, et al.; J. Am. Chem. Soc., vol. 115:2529–2531, (1993).
Persengiev, et al. Tissue–specific modulation of rat glucocorticoid receptor binding activity by melatonin. Experientia vol. 49(4):332–334, Jun. 3, 1993.
West et al. Melatonin levels are decreased in rheumatoid arthritis. J. Basic Clin. Physiol Pharmacol. vol. 3(1):33–40, Jan. 1992.

5,958,683

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: protein_bind
        (B) LOCATION: 1..16
        (D) OTHER INFORMATION: /bound_moiety= "RZR/ROR"
            /standard_name= "POTT"

(xi) SEQUENCE DESCRIPTION: SEQ ID NO:1:

GTAGGTCATG ACCTAC                                                        16

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: protein_bind
        (B) LOCATION: 1..19
        (D) OTHER INFORMATION: /bound_moiety= "VDR"

(xi) SEQUENCE DESCRIPTION: SEQ ID NO:2:

AGAGGTCAAG GAGGTCACT                                                     19

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: protein_bind
        (B) LOCATION: 1..19
        (D) OTHER INFORMATION: /bound_moiety= "RXR and RAR"

(xi) SEQUENCE DESCRIPTION: SEQ ID NO:3:

AGGGTTCACC GAAAGTTCA                                                     19

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:

(A) NAME/KEY: protein_bind
            (B) LOCATION: 1..16
            (D) OTHER INFORMATION: /standard_name= "CRUBPI"

(xi) SEQUENCE DESCRIPTION: SEQ ID NO:4:

AGAGGTCAAA AGGTCA                                                          16

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: protein_bind
        (B) LOCATION: 1..22
        (D) OTHER INFORMATION: /standard_name= "IP10"

(xi) SEQUENCE DESCRIPTION: SEQ ID NO:5:

TGACCTACTT ATAAGTAGGT CA                                                   22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: protein_bind
        (B) LOCATION: 1..22
        (D) OTHER INFORMATION: /standard_name= "DR8"

(xi) SEQUENCE DESCRIPTION: SEQ ID NO:6:

GTAGGTCACT ATAAGTAGGT CA                                                   22

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: protein_bind
        (B) LOCATION: 1..16
        (D) OTHER INFORMATION: /standard_name= "TREpalP0"

(xi) SEQUENCE DESCRIPTION: SEQ ID NO:7:

TCAGGTCATG ACCTGA                                                          16

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:

```
            (A) NAME/KEY: protein_bind
            (B) LOCATION: 1..19
            (D) OTHER INFORMATION: /standard_name= "DR5GT"

(xi) SEQUENCE DESCRIPTION: SEQ ID NO:8:

GTAGGTCATA AGTAGGTCA                                                    19

(2) INFORMATION FOR SEQ ID NO:9:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

NANNTRGGTC A                                                            11
```

SCREENING METHOD USING THE RZR RECEPTOR FAMILY

This is a 371 of PCT/EP95/01017, filed Mar. 18, 1994.

The current invention concerns the use of a receptor from the RZR/ROR receptor family or of a functional fragment thereof in a test of a compound for anti-autoimmune, anti-arthritic, anti-tumor, melatonin-like and/or melatonin-antagonistic activity and the production of a receptor ligand complex comprising said receptor or a functional fragment thereof and a ligand of said receptor. Described is also a method for testing compounds for said agonists or antagonists (screening for ligands) and the active compounds identified therewith.

INTRODUCTION

Small lipophilic substances like retinoic acid (RA), 1,25-dihydroxyvitaminD$_3$ (VD), thyroid hormone (T3) and steroid hormones regulate a number of developmental and physiological processes in vertebrates and in invertebrates by binding to specific receptors that function directly as transcription factors. These ligand-dependent transcription factors are members of the nuclear receptor superfamily.

The nuclear receptor superfamily also includes structurally related proteins for which no ligand has been identified yet and therefore are referred to as orphan receptors (O'Malley et al., Mol. Endocrinol. (1992), 6, 1259–1361). Examples of such orphan receptors are peroxisome-proliferator activated receptors (PPARs) and chicken ovalbumin upstream promoter transcription factor (COUP-TFs). Despite large diversity in function, two conserved zinc-finger motifs which are involved in binding to DNA appear in all members of this superfamily.

Recently, a novel orphan receptor family has been identified via a reverse transcription-polymerase chain reaction (RT-PCR) strategy (Becker-Andre et al., Biochem. Biophys. Res. Com. (1993), 194, 1371–1379; Becker-Andre et al., Keystone Symposium, Feb. 7–13, 1994, Taos, N. Mex., p.376). RZR/RORs are able to bind as monomers to their specific response elements, but they seem to interact with certain constellations of binding sites cooperatively as homodimers. RZR/RORs show constitutive transactivation and despite different approaches no ligands have been isolated so far for the RZR/ROR receptor family and therefore, it has been assumed, that RZR/RORs may provide constitutive rather than ligand-inducible transactivation.

Surprisingly, it has now been found, that melatonin is a natural ligand of the RZR/ROR receptor family. It was only known that melatonin is a ligand of a membrane receptor, which has been recently cloned from frog skin (Ebiswawa et al., Proc. Natl. Acad. Sci. USA (1994), 91, 6133–6137) and from mamalian tissues (Reppert et al., Neuron (1994), 13, 1177–1185). Melatonin is the major hormon of the pineal gland, but it is also produced in extrapinal tissues. It lightens skin color in amphibians by reversing the darkening effect of MSH (melanotropin). Melatonin is a transmitter of photoperiodic information and is a regulator of seasonal reproductive cycles in photoperiodic animals. It has been shown also that melatonin is involved in thermoregulation and neuroimmunoregulation (Fraschini and Reiter, Eds., Plenum Press N.Y., London 1991).

Melatonin has a short half life in animals and man and it is therefore surprising for melatonin to be a ligand of a nuclear receptor.

As a further surprise, synthetic chemical substances have also been identified as artificial ligands of the RZR/ROR receptor family. Said compounds are known and show anti-autoimmune, anti-arthritic and/or anti-tumor activity (EP-A-494047, EP-A-508955, EP-A-548017, EP-A-548018, CH-511877 and BE-753532). These properties can be demonstrated in vivo, for example in the adjuvant arthritis model in rats in accordance with Wiesenberg et al., Clin. Exp. Immunol. (1989), 78, 245 and the DMBA-tumor model in rats (Schmidt-Ruppin etal., Experentia (1973), 29, 823–825).

These compounds and the pharmaceutically acceptable salts thereof are known to have valuable pharmacological properties in the treatment of diseases of the rheumatoid type. Those diseases include, especially, rheumatoid arthritis, juvenile arthritis, ankylosing spondylitis, and other seronegative spondylarthritises, Colitis ulcerosa and Crohn's disease, and also reactive arthritises, collagen diseases, such as Lupus erythematosus and scleroderma, degenerative rheumatic diseases, extra-articular rheumatic and para-rheumatic diseases, for example gout, osteoarthritis and osteoporosis. Furthermore, compounds of this type have immuno-modulating and anti-tumor activities and, hence, can be administered generally in tumor therapy and in autoimmune based or related diseases such as multiple sclerosis, Hashimoto thyriditis, juvenile diabetes and psoriasis.

Nobody could expect or predict that these compounds function as ligands of the RZR/ROR receptor family, too. The anti-autoimmune, anti-arthritic and/or anti-tumor activity observed, implies that the binding of the ligand to the receptor enhances the affinity of the receptor to specific DNA regions (so called hormone response elements) in genes, which are involved in the regulation of cell proliferation and/or differentiation. The transcription of these response genes is either up or downregulated after binding of the ligand-receptor complex. Based on this novel observations it is now possible to use this receptor family for the screening of further compounds (ligands) having anti-autoimmune, anti-arthritic, anti-tumor, melatonin-like and/or melatonin-antagonistic activity.

DETAILED DESCRIPTION OF THE INVENTION

Thus the present invention preferably relates to the use of a receptor of the RZR/ROR receptor family or a functional fragment thereof in a test for identifying a compound with anti-autoimmune, anti-arthritic, anti-tumor, melatonin-like and/or melatonin-antagonistic activity.

In general, these compounds (ligands) can be tested for agonistic and antagonistic activity in respect to the RZR/ROR receptor family.

The RZR/ROR receptor family embraces nuclear receptors that consist of several domains, each domain having a specific function. Nuclear receptors generally act via suppression or activation of transcription after the binding of a ligand to the receptor. Members of the RZR/ROR receptor family show affinity to a certain kind of ligand. Individual members of the RZR/ROR family may, for example, be produced by alternative splicing of a common DNA coding for said receptors.

Functional fragments of these receptors are, e.g., constructs that have the same properties with respect to ligand selectivity, e.g., constructs comprising the ligand binding domain and the DNA binding domain of a receptor of the RZR/ROR receptor family but are devoid of other domains or wherein other protein fragments to address some special properties to the RZR/ROR have been inserted. Also included are fragments that are constructed by combination of the ligand binding domain with other fragments that all ow the decision whether a ligand is bound or not as, e.g., another DNA binding domain; or constructs wherein the ligand binding domain is connected via a spacer group to a solid carrier for fishing ligands.

Fragments of RZR/RORs including the functional ligand binding domain can also be labeled using one or more groups that can be identified easily, as for example a fluorescent, chemiluminescent or a radioactive group or can be connected to avidin, biotin, a reporter enzyme or any group easily detectable by spectroscopic or immunogenic methods like NMR, IR, UV, NMR, MS and ELISA. Constructs of this type can be used in the screening of compound libraries as described for example in Walter et al., TIBTECH (1993), 11, 247–254.

Most preferred members of the RZR/ROR receptor family are RZR/RORα, RZR/RORβ or RZR/RORγ (Hirose et al., Biochem, Biophys Res. Comm. (1994), 205, 1976–1983). RZR/RORs ca n be used as monomers or dimers including homodimers and heterodimers. Also possible are the splicing variants like RORα1 (Giguere et al, Genes and Development (1994), 8, 538–553) and the like.

The synthetical ligands known so far, and referred to above, have valuable pharmacological properties in the treatment of diseases of the autoimmune, rheumatoid and/or tumor type.

A further object of the invention is to provide a method for testing compounds for anti-autoimmune, anti-arthritic, anti-tumor, melatonin-like and/or melatonin-antagonistic activity, comprising
a) transfection of a suitable host with an expression cassette coding for a receptor of the RZR/ROR receptor family or a functional fragment thereof;
b) combination of one or more response elements for said receptor and a reporter gene and cotransfection of the host with this construct;
c) addition of the compound to be tested;
d) measurement of the expression of the reporter gene.

Receptors of the RZR/ROR receptor family or functional fragments thereof are as defined above.

Preferably, the host is free from endogenous RZR/ROR or is genetically modified to be free from RZR/ROR before being transfected with the expression cassette coding for a receptor of the RZR/ROR receptor family or a functional fragment thereof. A preferred host is for example a bacterial, fungal as e.g., yeast, insect or mammalian cell. Especially preferred are *Echerichia Coli, Saccharomyces cerevisiae* and Drosophila cells.

Expression cassettes for a receptor of the RZR/ROR receptor family or a functional fragment thereof usually contain a promoter operably linked to a DNA sequence coding for a receptor of the RZR/ROR receptor family or a functional fragment thereof and to a DNA sequence containing transcription termination signals.

Suitable promoter and terminator sequences are preferably chosen to be active in said host and are well known in the art. They can be combined with the structural gene and optionally with a marker group and other favorable elements by standard techniques in genetic engineering.

Nonlimiting examples are: the promoter of the TRP1 gene, the ADHI or ADHII gene, acid phosphatase (PHO5) gene, CUP1 gene, isocytochrome c gene, or a promoter of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinaseo genes, or a promoter of the yeast mating pheromone genes coding for the a- or α-factor.

Transfection protocols for the insertion of an expression cassette, e.g., via a plasmid or via integration into the genome, are of common knowledge and can easily be adapted to the cassette comprising a receptor of the RZR/ROR family or a functional fragment thereof.

The response elements are known and are usually chosen in accordance with the specificity of the DNA binding domain of the RZR/ROR used in the test. Suitable response elements for the RZR/ROR receptor family include for example the core half site having the DNA sequence T($A/G$) GGTCA.

Preferred are response elements suitable for RZR/RORα, as for example NANNT($A/G$)GGTCA.

The response element(s) is or are usually inserted via a short fragment with suitable restriction sites that is, e.g., synthesized on a DNA synthesizer with appropriate ends for the integration in or in the vicinity of the reporter gene using conventional means, as for example cutting the reporter gene with suitable restriction enzymes and inserting the response element. The wording "in or in the vicinity of the reporter gene" stands for a location capable of influencing the transcription of the reporter gene on binding the receptor. Due to the transcriptional activation properties of RZR/RORs, the response element is preferably inserted at a trans or cis transcriptional activation site of the reporter gene to regulate transcription if a suitable ligand has bound to the ligand binding domain.

The expression of reporter genes can be measured, e.g., on the transcriptional or translational level like the amount of a protein produced, an enzymatic activity or cell growth. Suitable reporter genes are well known in the art. Examples are chloramphenicol acetyltransferase (CAT), β-D-galactosidase (lacZ) or bacterial hybrid luciferase (luxAB).

A different approach in screening compounds for ligand activity is to generate a library consisting of a large amount of different compounds (compound library). The receptors, e.g. RZR/RORs or fragments thereof with an easily detectable group (see above), are incubated with this library and those compounds that are bound to receptors are identified. The construction of compound libraries is broadly described in literature as for example in Jung et al., Angewandte Chemie (1992), 104, 375–391 and for one bead one sequence libraries in Kerr et al., J. Am. Chem. Soc. (1993), 115, 2529–2531.

A further embodiment of the invention is a method for the production of a receptor ligand complex comprising incubating a receptor from the RZR/ROR receptor family or a functional fragment thereof with a compound showing anti-autoimmune anti-arthritic, anti-tumor, melatonin-like and/or melatonin-antagonistic activity.

Receptors from the RZR/ROR receptor family or a functional fragment thereof can be obtained as described above, e.g. via expression in a suitable host or via isolation from the natural surroundings (Becker-André et al., Biochem. Biophys. Res. Corn. (1993), 194, 1371–1379).

The incubation method depends on the method that provides the receptor. If, for example, the receptor is provided via expression in a suitable host, as described above, the test compounds can be added directly to the cell suspension or, if the compounds are unable to pass the cell membrane, suitable carriers have to be added or a cellfree system has to be used.

In case of screening compound libraries, the receptor is usually added to a solution or suspension comprising said library. If the receptor is fixed to an insoluble carrier like a bead, a little rod, foil or cellulose paper, it is also possible to add the compound library to the receptor, e.g. to add the library to a column comprising the fixed receptor.

The identification of the compounds that bind to the receptors (ligands) depends on how the compounds and/or the receptors are provided. In case of receptors that are expressed in a cell and that bind to a regulatory sequence of a reporter gene, the compound can be identified via the transcription or translation product of the reporter gene; or in case of screening compound libraries, e.g., an one bead one sequence library, the beads having bound receptor can be isolated and the ligand connected to the beads identified.

A further part of the invention concerns the use of a novel ligand that has been identified to bind to a receptor from the RZR/ROR receptor family or a functional fragment thereof as described above, in a method of treatment, especially in a method of treatment of autoimmune diseases, arthritic diseases, tumors, or diseases where usually melatonin or a melatonin agonist or antagonist is applied and more preferred in a method of treatment of autoimmune diseases, arthritic diseases and/or tumors.

Since there are no ligands with melatonin-antagonistic properties at the RZR/ROR receptor available so far, their pharmacological profile and their potential therapeutic value is currently unkknown.

Suitable ligands of RZR/ROR receptors are, for example, melatonin or melatonin derivatives as described for example in EP-585206.

Further compounds that bind to the RZR/ROR receptor family are for example those of formula (1) to (17)

(1)

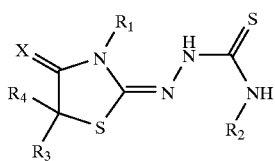

(2)

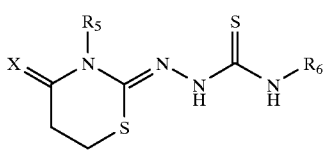

wherein $R_1$ and $R_5$ are $C_3$–$C_5$alkyl, $C_3$–$C_5$alk-2-en-1-yl or $C_3$–$C_5$alk-2-yn-1-yl; and especially allyl, methallyl and propinyl;

$R_2$ and $R_6$ are hydrogen, $C_1$–$C_5$alkyl, $C_3$–$C_5$alk-2-en-1-yl, $C_3$–$C_5$alk-2-yn-1-yl, aryl, aryl lower alkyl, saturated or unsaturated heterocyclyl lower alkyl or lower alkoxy carbonyl lower alkyl;

$R_3$ and $R_4$ are each independently of the other hydrogen, lower alkyl or together form lower alkylidene; X is oxo or sulfo; or a compound of formula (3)

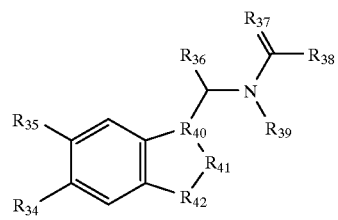

wherein $R_{34}$ and $R_{35}$ are independent of the other hydrogen, methoxy, or fluoro; $R_{36}$ is hydrogen or methoxycarbonyl, $R_{37}$ is oxo or sulfo; $R_{38}$ is hydrogen, $C_1$–$C_6$alkyl, cyclopropyl, cyloputyl, cyclopentyl, cyclohexyl, $C_1$–$C_6$alkyl substituted by Br, Cl, F or I phenyl, $C_1$–$C_3$alkyl-benzene, substituted or unsubstituted by halogen, indolyl, morpholino, methylmorpholino, amino, amino substituted with $C_1$–$C_4$alkyl, or 1-(2', 3', 4'-trimethoxy-benzyl) piperazine-methyl, 2-pyrrolidinone; $R_{39}$ is hydrogen, methyl or fluoro; $R_{40}$ is a carbon or nitrogen atom; $R_{41}$ is a carbon or nitrogen atom or a carbonyl group; $R_{42}$ is a carbon, nitrogen or sulfor atom or a vinylene group; the bond between $R_{40}$ and $R_{41}$ my be a single or double bond, with the proviso that it is a single bond if $R_{41}$ is a carbonyl group or $R_{40}$ is a nitrogen atom.

Also embraced are pro-drugs that are metabolized in vivo to give a compound as described above.

Methods for the synthesis of these compounds and examples for anti-autoimmune, anti-arthritic and/or anti-tumor activity of these compounds are given, for example in EP-447285, EP-A-494047, EP-506539, EP-A-508955, EP-527687, EP-530087, EP-A-548017, EP-A-548018, EP-562956, EP-578620, EP-A-585206, EP-591057, U.S. Pat. No. 5,283,343, U.S. Pat. No. 5,206,377, Depreux et al. (J. Med Chem (1994), 37, 3231–3239), Garrat & Vonhoff (Bioorganic & Medicinal Lett. (1994), 4, 1559–1565) and Copinga et al. (J. Med. Chem. (1993), 36, 2819–2898). Further examples for suitable compounds are:

(4)

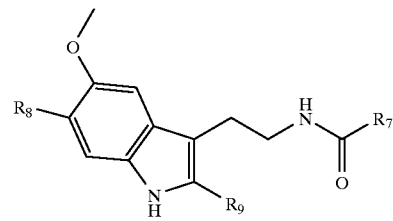

wherein $R_8$=hydrogen; $R_9$=bromo; and $R_7$=methyl; or $R_8$ =hydrogen; Rg =iodo; and $R_7$ =methyl; or $R_8$=chloro; $R_9$=hydrogen; and $R_7$=methyl; or $R_8$=hydrogen; $R_9$=methyl; and $R_7$=chloropropyl; or (5)
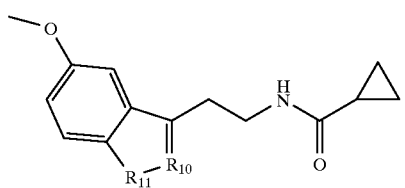

wherein $R_{10}$=CH; and $R_{11}$=sulfo or oxo; or $R_{10}$=oxo or NH; and $R_{11}$=NH; or (6)
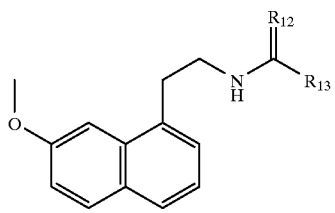

wherein $R_{12}$=oxo or sulfo; and $R_{13}$=NHCH$_2$CH$_2$CH$_3$; or $R_{12}$=oxo; and $R_{13}$=methyl; or (7)
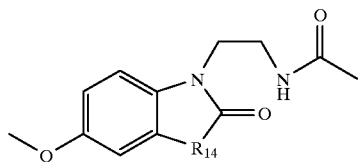

wherein $R_{14}$ is oxo or sulfo; or (8)
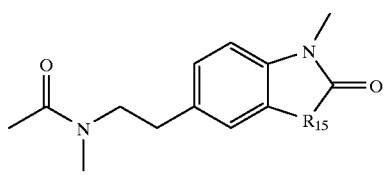

wherein $R_{15}$ is oxo or sulfo (9)
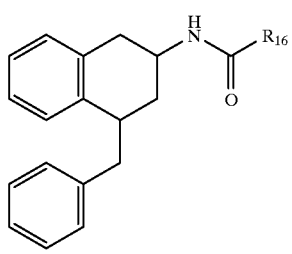

wherein $R_{16}$ is methly, ethyl or chlormethyl; or

(10)
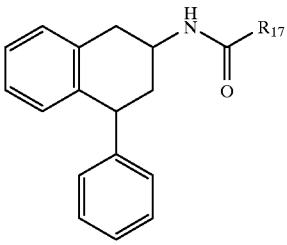

wherein $R_{17}$ is methly, ethyl or chlormethyl; or

(11)
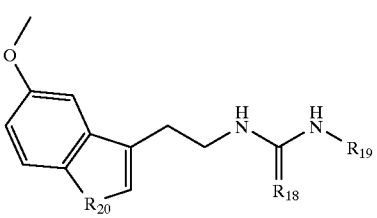

wherein $R_{20}$ is NH, CH=CH, oxo or sulfo; $R_{18}$ is oxo or sulfo; $R_{19}$ is hydrogen, methyl, ethyl or propyl; or

(12)
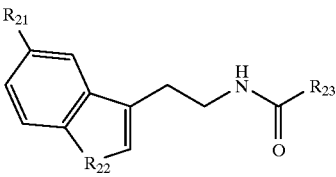

wherein $R_{21}$ is methoxy or hydrogen; $R_{22}$ is NH, CH=CH, sulfo, or oxo; and $R_{23}$ is methyl, cyclopropyl or cyclobutyl; or

(13)
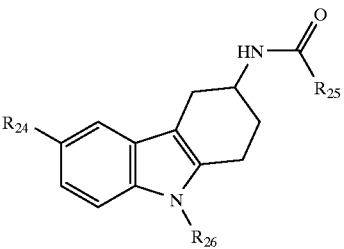

wherein $R_{24}$ is hydrogen or methoxy; $R_{25}$ is methyl, ethyl, propyl, CF$_3$, CH$_2$Br, CHBrCH$_2$CH$_3$, cyclopropyl, or cyclobutyl; or (14)

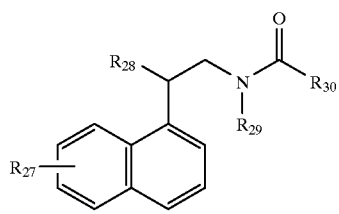

wherein $R_{27}$ is methoxy; $R_{28}$ is hydrogen or $COOCH_3$; $R_{29}$ is hydrogen, methyl or fluoro; and $R_{30}$ is hydrogen, methly, ethyl, butyl, propyl, pentyl, hexyl, isopropyl, $CH=CHCH_3$, cyclohexyl, $CH_2Br$, $CH_2I$, $CF_3$, $C_3H_6Cl$, phenyl, 3,5-dichlorobenzene, 2-indolyl, toluene, $CH(C_5H_5)_2$, $(CH_2)_2C_6H_5$, $(CH_2)_3C_6H_5$, methyl-morpholino, 1-(2', 3', 4'-trimethoxy-benzyl)piperazine-methyl, 2-pyrrolidinone, $SO_2CH_3$; or (15)

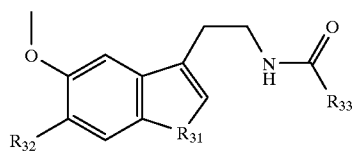

wherein
$R_{31}$ is NH, oxo, or sulfo; $R_{32}$ is hydrogen or fluoro; and $R_{33}$ is propyl, butyl, $CH_2I$, $CF_3$ or methyl; or (16)

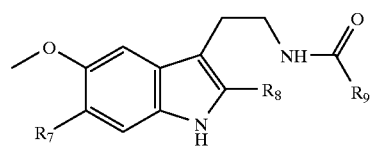

wherein $R_7$=hydrogen or $C_1$–$C_3$alkyl;
$R_8$=$C_1$–$C_6$alkyl, aryl, hydroxy aryl or halogen; and
$R_9$=$C_1$–$C_5$alkyl or halogen.

(17)

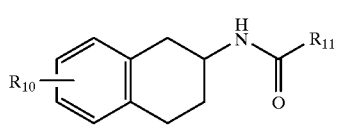

wherein $R_{10}$=hydrogen or methoxy; and
$R_{11}$=$C_1$–$C_3$alkyl, aryl, arylalkyl or $C_1$–$C_3$alkyl substituted with halogen.

Especially mentioned are compounds of formula (18)–(32)

(18)

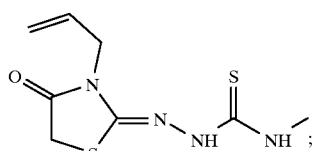

(19)

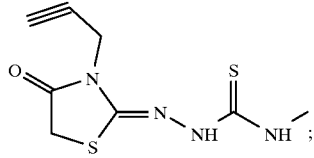

(20)

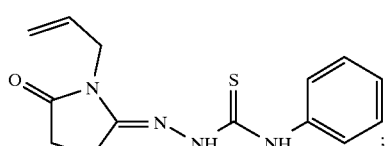

(21)

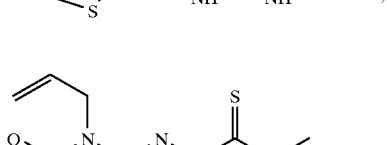

(22)

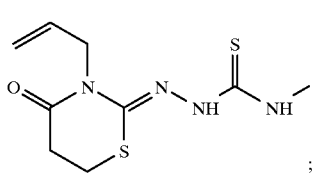

(23)

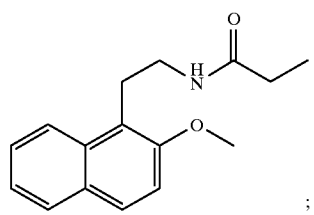

(23)

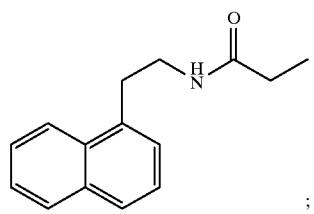

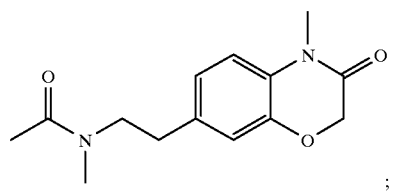

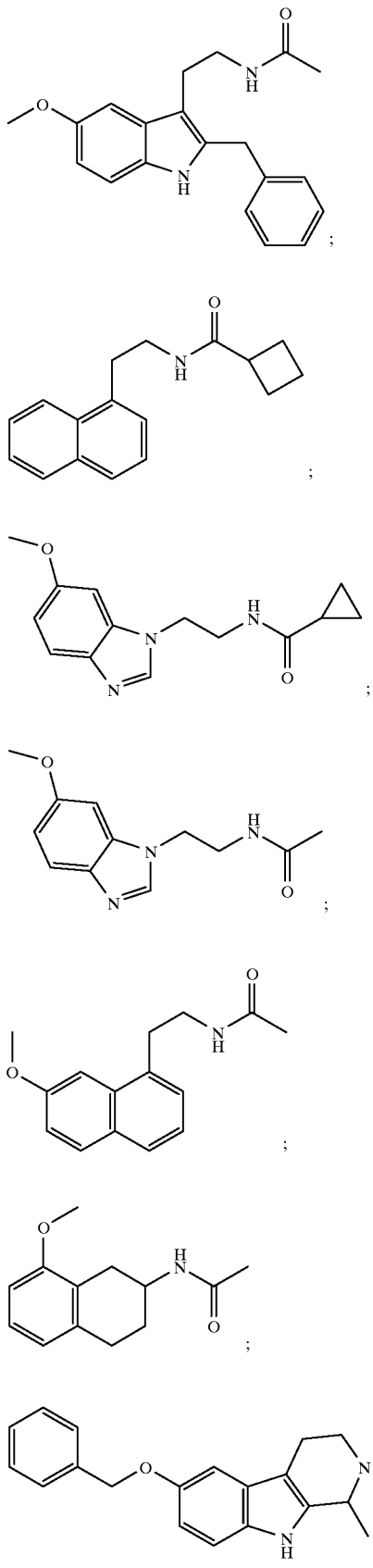

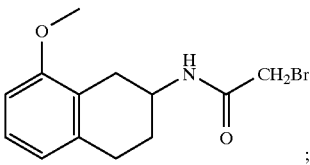

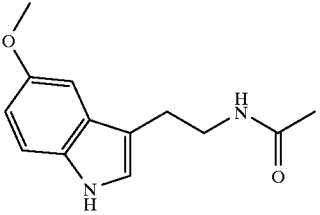

and

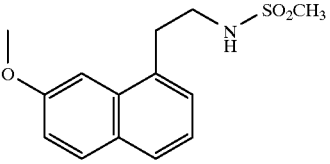

Also enclosed by the scope of the present invention is the use of a melatonin-antagonist or agonist, preferably, like compounds (1) to (3); more preferably (4) to (17); and most preferably (4) to (10) and (18) to (32); for the modification of the activity of the RZR/ROR receptor family and the use of one or more of these compound as an antagonist or agonist of the RZR/ROR receptor family.

EXAMPLES

Example 1

Construction Of The Expression System

The test for ligand induced activation is carried out essentially as described in Carlberg et al., Nature (1993), 361, 657–660.

The response elements for RZR/ROR are cloned as double stranded oligonucleotides with XbaI overhangs into the XbaI site upstream of the tk promoter in the CAT reporter plasmid pBLCAT2 (Luckow et al., Nucleic Acids Res. (1987), 15, 5490). This insert is synthesized on an automatic DNA synthesizer and the sequences for the response element of the top strand is given in SEQ ID NO:1

GTAGGTCATGACCTAC                    SEQ ID NO:1

Drosophila SL-3 cells ($2 \times 10^6$ per 60 mm Petri dish; J. Embryol. Expl. Morphol. (1972), 27, 353–365) are grown overnight in Schneider's medium (Gibco') supplemented with 15% charcoal-treated fetal calf serum. For transfection, liposomes were formed by incubating 5 µg reporter plasmid (with response element insert), 3 µg reference plasmid (pRSVβ-gal) and 1 µg of RZR/RORα expression vector (Carlberg et al., Nature (1993), 361, 657–660) with 11 µg N-(1-(2,3-di oleolyloxy)propyl)-N,N,N-trimethyl ammonium methyl sulfate (Boehringer-Mannheim) for 15 min. at room temperature in a total volume of 100 µl. After dilution with 0.9 ml Schneider's medium, the liposomes are added to the cells.

Example 2

Test Of Selectivity

Test compounds (dissolved in ethanol, test-concentration 1 µM, see table 1) that are known to be active or inactive in adjuvant arthritis (see table 1) are added to the cells 8 h after transfection with RZRα. After 40 h the cells are collected for the determination of the CAT activity (CAT assay, a standard technic of genetic engineering, see for example Gorman et at. Molec. Cel. Biol. (1982), 2, 1044–1051). The values given in table 1 represent the mean activation of CAT activities measured in three independent experiments, compared to the addition of pure solvent (ethanol).

To show the specific action of the inventive compounds, the experiments are carried out in parallel with the vitamin $D_3$ receptor (VDR) and retinoic acid receptors (RAR and RXR) using SEQ ID NO:2 and 3 as response element (Carlberg et al., Nature (1993), 361, 657–660).

```
AGAGGTCAAGGAGGTCACT      SEQ ID NO:2

AGGGTTCACCGAAAGTTCA      SEQ ID NO:3
```

Example 4

Test Of Recognition Sites

The test as described in example 2 is repeated using compound (3) on RZR/ROR and the following response elements:

```
AGAGGTCAAAAGGTCA              SEQ ID NO:4

TGACCTACTTATAAGTAGGTCA        SEQ ID NO:5

GTAGGTCACTATAAGTAGGTCA        SEQ ID NO:6

TCAGGTCATGACCTGA              SEQ ID NO:7

GTAGGTCATAAGTAGGTCA           SEQ ID NO:8
```

The increase of CAT activity (see example 1) compared to solvent is given in table 3

TABLE 1

| Compound | Fold stimulation of CAT expression | | | | activity in adjuvant arthritis | Response element |
|---|---|---|---|---|---|---|
| | RZRα | VDR | RAR | RXR | | |
| (3) | 3.25 | 1.2 | 1.1 | 1.0 | + | SEQ 1 |
| (4) | 4.5 | 1.2 | 1.2 | 1.0 | + | SEQ 1 |
| (5) | 5.2 | 1.0 | 1.0 | 0.9 | + | SEQ 1 |
| (6) | 5.0 | 1.2 | 0.9 | 1.0 | + | SEQ 1 |
| melatonin | 4.8 | 1.1 | 1.1 | 1.2 | ? | SEQ 1 |
| vitamin D | 0.9 | 10.3 | 1.0 | 1.0 | − | SEQ 2 |
| all trans RA | 1.2 | 1.0 | 10.4 | 1.5 | − | SEQ 3 |
| 9-cis RA | 1.1 | 2.1 | 1.4 | 5.3 | − | SEQ 3 |

This clearly demonstrates, that the response of the RZR/RORα is specific for a certain class of compounds.

Example 3

Test Of Dose Response

Various amounts of the test compounds are added to the test system containing compound (3), (4), (6) or melatonin according to table2, RZR/RORα and SEQ ID NO:1 as described in example 2 (see table 2).

TABLE 2

| Concentration of ligand [nM] | Fold stimmulation using | | | |
|---|---|---|---|---|
| | (3) | (4) | (6) | melatonin |
| 1000 | 4.2 | 4.1 | 5.1 | 4.8 |
| 333 | 4.4 | 4.0 | 5.2 | 5.0 |
| 100 | 4.3 | 4.2 | 5.0 | 5.0 |
| 33 | 4.15 | 4.1 | 4.3 | 5.0 |
| 10 | 2.9 | 4.2 | 2.3 | 3.0 |
| 3.3 | 1.8 | 4.0 | 1.4 | 2.1 |
| 1 | 1.3 | 2.5 | 1.1 | 1.0 |
| 0.33 | 1.1 | 1.7 | 1.0 | 1.0 |
| 0.1 | 0.9 | 1.3 | 1.1 | 1.0 |
| 0 | 1.0 | 1.0 | 1.0 | 1.0 |

This example demonstrates the high affinity of compounds 3, 4, 6 and melatonin to the RZR/RORα receptor, when applied in the nanomolar range.

Specificity (Table 1) and affinity (Table 2) of the given test compounds were comparable using either the RZR/RORα or RZRβ.

TABLE 3

| SEQ ID NO | Fold stimmulation compared to solvent |
|---|---|
| 4 | 6.8 |
| 5 | 1.75 |
| 6 | 5.8 |
| 7 | 6.2 |
| 8 | 1.8 |

This example demonstrates that the response is specific for a certain sequence in the response element.

We claim:

1. A method for identifying compounds having anti-autoimmune, anti-arthritic, anti-tumor or melatonin-antagonistic activity comprising the steps of:
   contacting the compound to be tested with a receptor of the RZR/ROR receptor family said receptor being combined with a response element; and
   measuring a signal produced by the response element in response to the binding of the compound to the receptor, wherein the compounds are identified.

2. The method according to claim 1, wherein the receptor is RZR/RORα, RZR/RORβ or RZR/RORγ.

3. The method according to claim 1, wherein the receptor is RZR/RORα.

4. The method according to claim 1, wherein the receptor is a monomer or dimer.

5. A method for testing compounds for anti-autoimmune, anti-arthritic, anti-tumor or melatonin-antagonistic activity comprising the steps of incubating a compound library with the receptor according to claim 1 and selecting the compounds that bind to said receptor.

6. A method for testing compounds for anti-arthritic, anti-autoimmune, anti-tumor, or melatonin-antagonistic activity comprising the steps of:
   a) transfection of a host with an expression cassette coding for a receptor according to claim 1;
   b) combination of one or more response elements for said receptor and a reporter gene and cotransfection of the host with this construct;
   c) addition of the compounds to be tested; and
   d) measurement of the expression of the reporter gene.

7. The method according to claim 6, wherein RZR/ROR is ZR/RORα, RZR/RORα or RZR/RORγ.

8. The method according to claim 6, wherein RZR/ROR is RZR/RORα.

9. A method according to claim 6, wherein the host is free of endogenous RZR/ROR prior to transfection with the expression cassette.

10. The method according to claim 6, wherein the host is a bacterial, fungal, insect or mammalian cell.

11. The method according to claim 6, wherein the host is a yeast or Drosophila cell.

12. The method according to claim 6, wherein the response element is specific for RZR/ROR.

13. The method according to claim 6, where the response element comprises the DNA sequence T(A/G)GGTCA.

14. A method according to claim 6, wherein the expression of the reporter gene is measured on the transcriptional or translational level.

15. The method according to claim 6, wherein the reporter gene is selected from the group consisting of chloramphenicol acetyltransferase (CAT), lacZ and bacterial hybrid luciferase (luxAB).

16. A method for the production of a receptor ligand complex comprising the steps of incubating a receptor according to claim 1 with a compound showing anti-autoimmune, anti-arthritic, anti-tumor or melatonin-antagonistic activity.

17. The method according to claim 16, wherein the receptor is RZR/RORα, RZR/RORβ or RZR/RORγ.

18. The method according to claim 16, wherein the is RZR/RORα.

19. The method according to claim 16, wherein the receptor is a monomer or dimer.

20. A method for the modification of the activity of the RZR/ROR receptor family comprising the steps of contacting a melatonin-antagonist or agonist to said receptor family wherein the receptor family activity is modified.

21. A method of antagonizing or agonizing the RZR/ROR receptor family comprising contacting the receptor family with the melatonin-antagonist or agonist according to claim 20.

22. The method according to claim 21, wherein the compound is melatonin or a melatonin derivative.

23. A method for identifying compounds which modify the RZR/ROR receptor family comprising the steps of:
   contacting a compound of formula (1), (2) or (3)

(1)

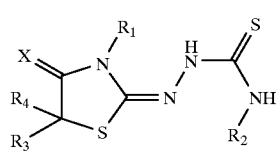

-continued

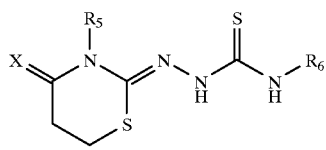
(2)

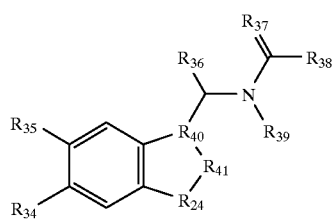
(3)

wherein $R_1$ and $R_5$ are $C_3$–$C_5$alkyl, $C_3$–$C_5$alk-2-en-1-yl or $C_3$–$C_5$alk-2-yn-1-yl; and especially allyl, methallyl and propinyl;

$R_2$ and $R_6$ are hydrogen, $C_1$–$C_5$alkyl, $C_3$–$C_5$alk-2-en-1-yl, $C_3$–$C_5$alk-2-yn-1-yl, aryl, aryl lower alkyl, saturated or unsaturated heterocyclyl lower alkyl or lower alkoxy carbonyl lower alkyl;

$R_3$ and $R_4$ are each independently of the other hydrogen, lower alkyl or together form lower alkylidene;

X is oxo or sulfo;

$R_{34}$ and $R_{35}$ are independent of the other hydrogen, methoxy, or fluoro;

$R_{35}$ is hydrogen or methoxycarbonyl, $R_{37}$ is oxo or sulfo;

$R_{38}$ is hydrogen, $C_1$–$C_6$alkyl, cyclopropyl, cycloputyl, cyclopentyl, cyclohexyl, $C_1$–$C_6$alkyl substituted by Br, Cl, F or I, phenyl, $C_1$–$C_3$alkyl-benzene, substituted or unsubstituted by halogen, indolyl, morpholino, methylmorpholino, amino, amino substituted with $C_1$–$C_4$alkyl or 1-(2', 3', 4'-trimethoxybenzyl) piperazine-methyl, 2-pyrrolidinone;

$R_{39}$ is hydrogen, methyl or fluoro;

$R_{40}$ is a carbon or nitrogen atom;

$R_{41}$ is a carbon or nitrogen atom or a carbonyl group;

$R_{42}$ is a carbon, nitrogen or sulfur atom or a vinylene group;

the bond between $R_{40}$ and $R_{41}$ may be a single or double bond, with the proviso that it is a single bond if $R_{41}$ is a carbonyl group or $R_{40}$ is a nitrogen atom, with a receptor of the RZR/ROR receptor family, said receptor being combined with a response element; and measuring a signal produced by the response element in response to the binding of the compound to the receptor, wherein the compounds are identified.

* * * * *